(12) United States Patent
Levine et al.

(10) Patent No.: US 9,395,365 B2
(45) Date of Patent: Jul. 19, 2016

(54) DETECTION OF INFECTIOUS DISEASE IN A HUMAN OR ANIMAL BY MEASURING SPECIFIC PHAGOCYTOSIS IN A THIN FILM SAMPLE OF THEIR ANTICOAGULATED BLOOD

(75) Inventors: Robert A. Levine, Guilford, CT (US); Stephen C. Wardlaw, Lyme, CT (US)

(73) Assignee: Abbott Point of Care, Inc., Princeton, NJ (US)

(*) Notice: Subject to any disclaimer, the term of this patent is extended or adjusted under 35 U.S.C. 154(b) by 1092 days.

(21) Appl. No.: 12/417,296

(22) Filed: Apr. 2, 2009

(65) Prior Publication Data
US 2010/0255509 A1  Oct. 7, 2010

(51) Int. Cl.
| | |
|---|---|
| *C12Q 1/00* | (2006.01) |
| *C12Q 1/68* | (2006.01) |
| *G01N 33/53* | (2006.01) |
| *G01N 30/00* | (2006.01) |
| *G01N 33/569* | (2006.01) |
| *C12Q 1/04* | (2006.01) |
| *G01N 33/50* | (2006.01) |
| *G01N 33/543* | (2006.01) |
| *G01N 15/14* | (2006.01) |
| *G01N 15/00* | (2006.01) |

(52) U.S. Cl.
CPC ............ *G01N 33/56911* (2013.01); *C12Q 1/04* (2013.01); *G01N 33/5094* (2013.01); *G01N 33/5432* (2013.01); *G01N 15/1475* (2013.01); *G01N 2015/008* (2013.01)

(58) Field of Classification Search
CPC ....... A61K 39/04; A61K 39/07; A61K 39/08; A61K 39/12; A61K 39/025; A61K 39/40; A61K 39/42; A61K 39/0208; A61K 39/0216; A61K 39/0225; A61K 2039/02; A61K 2039/60; A61K 2039/64; A61K 2300/00; C12Q 1/00; C12Q 1/689; C12Q 2537/10; C12Q 2537/01; C12Q 2537/25; C12Q 2537/49; C12Q 2537/55; C12Q 2537/37; C12Q 2537/143; C12Q 2563/107; G01N 15/00; G01N 21/6428; G01N 21/6447; G01N 2001/00; G01N 2021/00; G01N 2033/00

See application file for complete search history.

(56) References Cited

U.S. PATENT DOCUMENTS

| | | | |
|---|---|---|---|
| 4,581,334 A | 4/1986 | Kirchanski et al. | |
| 5,043,267 A | 8/1991 | Richards | |
| 5,965,702 A | 10/1999 | Robinson et al. | |
| 5,985,595 A * | 11/1999 | Krider et al. | 435/34 |
| 6,350,613 B1 * | 2/2002 | Wardlaw et al. | 436/10 |
| 2004/0197769 A1 * | 10/2004 | Wong et al. | 435/5 |
| 2007/0087442 A1 | 4/2007 | Wardlaw | |

FOREIGN PATENT DOCUMENTS

WO    WO 996349    * 12/1999    ............. G01N 33/68

OTHER PUBLICATIONS

George Babock, "Quantitation of Phagocytosis B Confocal Microscopy", Methods in Enzymology, Academic Press, Inc., vol. 307, pp. 319-328, Jan. 1999.

* cited by examiner

*Primary Examiner* — J. Hines
(74) *Attorney, Agent, or Firm* — O'Shea Getz P.C.

(57) ABSTRACT

A method for performing a target analyte assay of a thin film anticoagulated blood sample, wherein the target analyte is the presence or absence of specific phagocytosis and/or binding of particles coated with a particular antigen or antigens by white blood cells present in the anticoagulated blood sample, wherein the particles are coated with the particular antigen or antigens, which antigens are similar or identical to antigens expressed by a defined pathogenic infectious agent of interest.

11 Claims, 1 Drawing Sheet

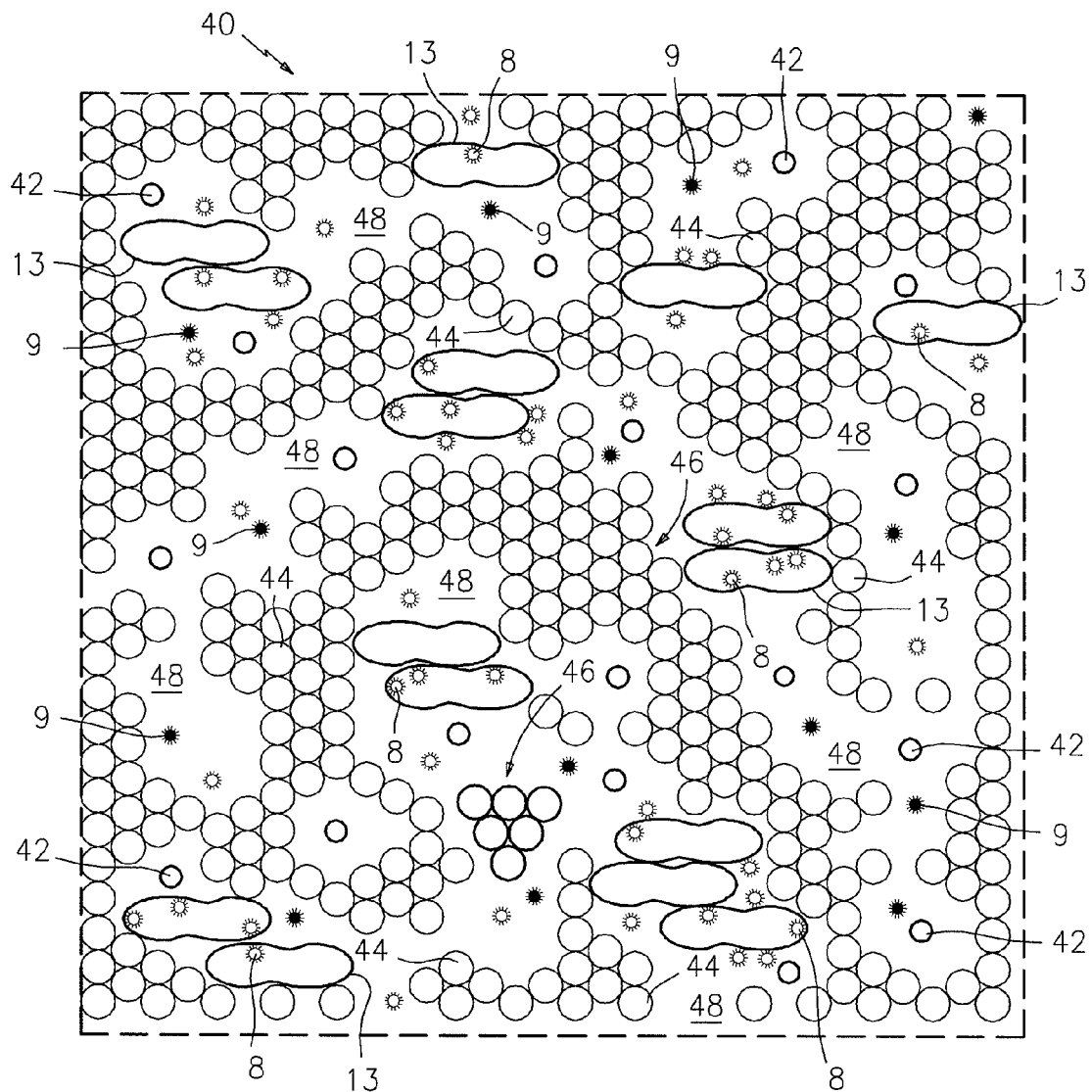

DETECTION OF INFECTIOUS DISEASE IN A HUMAN OR ANIMAL BY MEASURING SPECIFIC PHAGOCYTOSIS IN A THIN FILM SAMPLE OF THEIR ANTICOAGULATED BLOOD

BACKGROUND OF THE INVENTION

1. Technical Field

This invention relates to a method for performing a target analyte assay of a thin film anticoagulated blood sample, where the target analyte is the presence or absence of specific phagocytosis and/or binding of particles coated with a particular antigen or antigens by white blood cells, which blood sample contains the white blood cells present in the anticoagulated blood sample, and detectable first type particles coated with the particular antigen or antigens present on the surface which antigens are similar or identical to the antigens expressed by the defined pathological agent. More particularly, the present invention relates to electronic detection, quantization and characterization of phagocytosis and/or binding of detectable substances in human and animal biological fluids such as whole blood, or other fluids containing white blood cells, which characterization is performed in a thin chamber on a quiescent thin film fluid sample containing white blood cells, said chamber having at least two parallel planar walls, at least one of which is transparent. Lyme disease is used only as an example of one infectious disease that can be detected by this process. The present invention applies to all infectious agents that are combated by the biologic process of phagocytosis, some examples being gonorrhea or pneumococcal infection, as well as others.

2. Background Information

U.S. Pat. No. 5,985,595 Krider et al relates to diagnostic tests for the rapid detection of the presence of pathogens in human or animal blood. The blood sample being examined is spread on slides, air dried, fixed, stained and examined using a microscope. This patent is incorporated herein by reference in its entirety.

It would be desirable to be able to perform the diagnostic tests for the presence of the pathogens described in Krider et al in a more rapid and more simple manner that does not require that the sample be spread on slides, air dried, fixed, stained or examined with a microscope by a technician and that can be performed at the point of care.

SUMMARY OF THE INVENTION

This invention relates to a method for assaying an anticoagulated whole viable blood sample for the presence or absence of specific phagocytosis by white blood cells of added detectable particles, the first type being coated with specific antigens such as those found on Borrelia burgdorferi bacteria, and the second type of particles being similar in composition and size to the first particles but lacking the specific antigens and being distinguishable from the first particles by virtue of their color or fluorescence. Generally speaking, sodium citrate or heparin are employed as anticoagulants for such assays, although any anticoagulant that does not impair phagocytosis may be employed. The antigens for the detection of Lyme disease are described in the cited patent, U.S. Pat. No. 5,985,595, Krider et al. The presence or absence of specific phagocytosis of those particles will define the presence or absence of a recent or active infection such as Lyme disease in the sample donor's blood.

The method of this invention utilizes an electronic photometric microscopic analysis of the blood sample involving electronic imaging or scanning of the sample. The method involves placing the incubated blood sample, as described below, in a test chamber of predetermined and fixed thickness so as to produce a thin layer of the blood sample in the chamber. At least one wall of the chamber is transparent so that the sample can be observed in the chamber. In certain cases both the top and bottom walls of the chamber are transparent. The thickness of the chamber can range from $3\mu$ to $25\mu$. When anticoagulated whole blood is being analyzed the chamber should be preferably $4\mu$-$6\mu$ thick so as to obtain a thin film monolayer of the blood sample, which monolayer contains both white blood cells and red blood cells. The monolayer blood sample in the chamber will be imaged for the presence or absence of white blood cells that have bound or ingested the first detectable particles which are coated with an antigen that is specific to the target Lyme disease analyte, i.e., a Borrelia bacteria. The blood sample will also contain a similar number of second detectable particles, identical in size and composition to the first particles except for distinguishable color or fluorescence, which are not coated with a Lyme disease analyte-specific antigen. Lyme disease is used only as an example of one disease that may be detected using this method and when the term "Lyme" is used any infectious disease process that is characterized by alterations in phagocytosis may be substituted. The first and second particles will be characterized by different detectable signals such as color and or fluorescence so that they can be distinguished one from the other. The particles should otherwise be the same in size and composition, differing only by the presence or absence of the target antigen or antigens, since size and composition can affect phagocytosis. The particles to be used as type one and type two particles are both ideally identically sized in a range from about 1 to 3 microns in diameter, which is a size that permits easy detection and optimal phagocytosis by white blood.

The mixture of blood and the particles will be incubated for a predetermined time, optimally at body temperature, using heparin or sodium citrate as the anticoagulant of choice, for a time period of minutes to an hour, and then the blood sample will be placed in the analysis chamber. Since phagocytosis will have already been accomplished, thinner chambers slightly compressing the white blood cells will permit more discrimination of phagocytosed particles. In humans, a chamber height of 4 to 6 microns functions well. Alternatively, the blood may be added directly to the chamber which chamber has the anticoagulants and particles already in it and the incubation step is performed in situ and then the sample is read. In this case the chamber should be sufficiently sized so that the white blood cells can perform their phagocytosis without significant mechanical impediments. The chamber height chosen will depend upon the species being tested and the size of their viable phagocytes. The chamber will then be imaged to determine whether any of the first detectable particles have been ingested into white blood cells or are attached to the surface of white blood cells in the sample. The imaging will also determine whether any of the second detectable particles have been phagocytosed or bound by white blood cells in the sample. The comparison of the amount of particles of each type that are bound to and/or ingested will be used to indicate the presence or absence of recent or active infection or the blood's source with the target pathogen.

In order to be able to ensure the functionality of the assay, it is essential that experiments are run to determine the normal range for the number of particles of each type that are ingested per white blood cell in healthy non-Lyme disease exposed populations of the species being tested. If no particles or too few particles (defined as a number below the user defined normal range) of both type one particles and type two particles are phagocytosed, the test is invalid and such invalidity may be due dead or incompetent white blood cells or inadequate incubation conditions. If normal amounts of the first and second detectable particles are found to be phagocytosed by white blood cells, then that is an indication of the absence of Lyme disease, or other target pathogen. If more than normal amounts of the first type of particle relative to the second type particles are bound or ingested by leukocytes, then this indicates a positive test for the presence of active or recent infection with Lyme disease. If greater amounts of type one particles than type two particles are ingested but both amounts are within the normal range the test is inconclusive. If both the first and second detectable particles are found to be phagocytosed by white blood cells in less than normal amounts, then that is an indication of an invalid test. If both first and second detectable particles are found to be phagocytosed by white blood cells in amounts greater than normal, then this is an indeterminate result indicating increased phagocytosis due to unknown cause. Such a result can have important clinical utility but may not be used to indicate the presence or absence of the specific disease process being tested for.

DESCRIPTION OF THE DRAWINGS

FIG. 1 is a plan view of a portion of a test sampling chamber formed in accordance with this invention which contains an incubated anticoagulated whole blood sample which contains the first and second detectable particles used in performing the testing method of this invention.

DETAILED DESCRIPTION OF THE INVENTION

Referring now to FIG. 1, there is shown in plan view a portion of a sampling chamber 40 which contains a thin monolayer film sample of anticoagulated whole blood that has been incubated with the detection particles. In this case, the chamber 40 has a transparent upper surface so that the blood sample can be electronically or photometrically imaged. The thin film blood sample is contained in a sampling chamber which is provided with beads 42 that provide the desired thickness of the chamber 40, which in this case is about 6μ. The thin film of blood includes red blood cells 44, red blood cell clumps or rouleaux 46, plasma cell-free lacunae 48, and white blood cells 13. The blood sample also includes two detectable particles 8 and 9. The particles 8 are coated with the antigen or antigens specific to the target Lyme disease analyte, and the particles 9 are not coated with the target analyte-specific antigen(s). The particles 8 and 9 are differentially detectable in the sample when it is imaged.

FIG. 1 shows the results of a positive test for the presence of Lyme disease in the blood sample being tested. It will be noted that many of the white cells 13 in the blood sample have phagocytosed the Lyme disease-specific particles 8, and that none of the nonspecific particles 9 have been phagocytosed by any white cells 13. If the test were negative, none or relatively few of the white cells would have phagocytosed the particles 8 since there would be no Lyme disease bacterial analyte present in the blood sample, and if the test were inconclusive, then both the particles 8 and 9 would have been phagocytosed by the white blood cells 13 to a similar extent.

Ratios between the percentage or absolute number of cells containing phagocytosed particles of both types will be used to define positivity and negativity as well as validity of the assay. These ratios and/or percentages of cells containing particles of both types may further be sub-characterized by cell type, such as neutrophils or monocytes, both of which are capable of performing phagocytosis. Ratios of the percentage and or number of particles of each type ingested may also be performed to calculate results to define positivity and negativity as well as validity of the assay.

It will be appreciated that, while the specific example of a use of the method of this invention relates to the detection of Lyme disease in one's blood, it could also be used to detect the presence of other infectious pathogens, such as *S. pneumoniae*, which causes pneumonia, and *Neisseria gonorrhoea*, which causes gonorrhea, for example. These pathogens and others are susceptible to being phagocytosed by white blood cells also.

Since many changes and variations of the disclosed embodiment of the invention may be made without departing from the inventive concept, it is not intended to limit the invention except as required by the appended claims.

What is claimed is:

1. A method for performing a target analyte assay of a thin film monolayer sample of anticoagulated viable whole blood to determine a presence or absence of a blood donor's recent exposure or active infection with a defined pathogenic agent, wherein the target analyte is the presence or absence of specific phagocytosis and/or binding of particles coated with a particular antigen or antigens by white blood cells contained in said blood sample, said method comprising the steps of:
    mixing and incubating said blood sample with first detectable particles which are coated with an antigen that is specific to said target analyte, and with second detectable particles which are not coated with said antigen in said incubated mixture, and which second particles are distinguishable from the first particles on the basis of color or fluorescence, or both, so as to create an incubated mixture of said blood sample, said first particles, and said second particles, wherein the first and second particles are distinguishable from one another within the mixture;
    providing a sample chamber having a through plane thickness of between 3 and 25 μm;
    filling said chamber with said blood sample mixture;
    optically imaging said blood sample mixture within said chamber using an electronic photometric microscope device to determine an amount of any of said first particles which have been phagocytosed by individual white blood cells, and to determine an amount of any of said second particles which have been have been phagocytosed by individual white blood cells; and
    determining the presence or absence of the blood donor's recent exposure or active infection with the defined pathogenic agent, based on the determined amount of said first particles phagocytosed by individual white blood cells, and the determined amount of said second particles phagocytosed by individual white blood cells.

2. The method of claim 1, further comprising the step of determining the validity of the assay.

3. The method of claim 1, wherein the defined pathogenic agent is a *Borrelia* bacteria which is indicative of the presence of Lyme disease.

4. The method of claim 1, wherein said chamber has a through plane thickness of about 6 μm.

5. The method of claim 1, wherein the first particles and the second particles are sized to permit phagocytosis by white blood cells.

6. The method of claim 1, wherein the first particles and the second particles each have a diameter in the range of about one to three microns (1-3 μm).

7. A method for performing a target analyte assay of a thin film monolayer sample of anticoagulated viable whole blood to determine a presence or absence of a blood donor's recent exposure or active infection with a defined pathogenic agent, wherein the target analyte is the presence or absence of specific phagocytosis and/or binding of particles coated with a particular antigen or antigens by white blood cells contained in said blood sample, said method comprising the steps of:

mixing and incubating said blood sample with first detectable particles which are coated with an antigen that is specific to said target analyte, and with second detectable particles which are not coated with said antigen in said incubated mixture, and which second particles are distinguishable from the first particles on the basis of color or fluorescence, or both, so as to create an incubated mixture of said blood sample, said first particles, and said second particles, wherein the first and second particles are distinguishable from one another within the mixture;

providing a sample chamber having a through plane thickness of between 3 and 25 µm;

filling said chamber with said blood sample mixture;

optically imaging said blood sample mixture within said chamber using an electronic photometric microscope device to determine an amount of any of said first particles which have been bound by individual white blood cells; and determining the presence or absence of the blood donor's recent exposure or active infection with the defined pathogenic agent, based on the determined amount of said first particles bound by individual white blood cells.

8. The method of claim 1, further including providing a range of values representative of a number of first particles that are phagocytosed by white blood cells within each of a plurality of given sample volumes, which sample volumes are taken from a population of blood donors that have not been recently exposed or actively infected with the defined pathogenic agent, and further including providing a range of values representative of a number of second particles that are phagocytosed by white blood cells within each of the plurality of given sample volumes.

9. The method of claim 1, wherein the determining step includes comparing the determined amount of said first particles phagocytosed by individual white blood cells and the determined amount of said second particles phagocytosed by individual white blood cells to one another.

10. The method of claim 9, wherein the determining step further includes at least one of comparing the determined amount of said first particles phagocytosed by individual white blood cells to a first predetermined value, or comparing the determined amount of said second particles phagocytosed by individual white blood cells to a second predetermined value.

11. The method of claim 1, further comprising the step of determining the validity of the assay by at least one of comparing the determined amount of said first particles phagocytosed by individual white blood cells to a first predetermined value, or comparing the determined amount of said second particles phagocytosed by individual white blood cells to a second predetermined value.

* * * * *